US012642886B2

(12) United States Patent
Lichtenhan

(10) Patent No.: US 12,642,886 B2
(45) Date of Patent: Jun. 2, 2026

(54) POSS VISCOELASTIC HEMOSTATIC AGENTS

(71) Applicant: Hybrid Plastics, Incorporated, Hattiesburg, MS (US)

(72) Inventor: Joseph D. Lichtenhan, Petal, MS (US)

(73) Assignee: Hybrid Plastics, Incorporated, Hattiesburg, MS (US)

( * ) Notice: Subject to any disclaimer, the term of this patent is extended or adjusted under 35 U.S.C. 154(b) by 832 days.

(21) Appl. No.: 17/599,369

(22) PCT Filed: Mar. 30, 2020

(86) PCT No.: PCT/US2020/025727
§ 371 (c)(1),
(2) Date: Sep. 28, 2021

(87) PCT Pub. No.: WO2020/205740
PCT Pub. Date: Oct. 8, 2020

(65) Prior Publication Data
US 2022/0211903 A1 Jul. 7, 2022

Related U.S. Application Data

(60) Provisional application No. 62/826,132, filed on Mar. 29, 2019.

(51) Int. Cl.
*A61L 26/00* (2006.01)

(52) U.S. Cl.
CPC ....... *A61L 26/0095* (2013.01); *A61L 26/0004* (2013.01); *A61L 26/0019* (2013.01); *A61L 26/0023* (2013.01); *A61L 2300/418* (2013.01); *A61L 2400/04* (2013.01)

(58) Field of Classification Search
CPC ............. A61L 26/0095; A61L 26/0004; A61L 26/0019; A61L 26/0023; A61L 2300/418; A61L 2400/04
See application file for complete search history.

(56) References Cited

U.S. PATENT DOCUMENTS

2016/0325011 A1* 11/2016 Iwama ................ A61L 26/0066
2018/0271898 A1* 9/2018 Basadonna .......... A61K 8/0208

OTHER PUBLICATIONS

Lichtenhan et al.; The thrombogenic activity of POSS silanols; Royal Society of Chemistry; Dalton Trans., 2017, 46, 8788 (Year: 2017).*
Rushford; Potential Applications of Polyhedral Oligomeric Silsesquioxanes (POSS) as a Clotting Agent, Drug Delivery Carrier, and Tissue Engineering Material; ProQuest LLC; University of Mississippi Medical Center; Jackson, Mississippi; 2017 (Year: 2017).*
Lichtenhan et al.; The thrombogenic activity of POSS silanols; Royal Society of Chemistry; Dalton Transactions, 2017, 46, 8788-8796. (Year: 2017).*
Trabattoni et al.; A new kaolin-based haemostatic bandage compared with manual compression for bleeding control after percutaneous coronary procedures; European Society of Radiology; Eur Radiol (2011) 21:1687-1691. (Year: 2011).*
Bhattad; Review on viscosity measurement: devices, methods and models; Springer; Journal of Thermal Analysis and Calorimetry (2023) 148:6527-6543. (Year: 2023).*
Rushford KL "Potential Applications of Polyhedral Oligomeric Silsesquioxanes (POSS) as a Clotting Agent, Drug Delivery Carrier, and Tissue Engineering Material" Dissertation University of Mississippi Medical Center, Oct. 2017, pp. 1-24.
Lichtenhan JD, et al. "The Thrombogenic Activity of POSS Silanols" Dalton Trans. 2017, vol. 46, No. 27, pp. 8788-8796.
ISA/US, PCT/US2020/025727, International Search Report, Jun. 19, 2020, 2 pages.

* cited by examiner

*Primary Examiner* — Robert A Wax
*Assistant Examiner* — John W Lippert, III
(74) *Attorney, Agent, or Firm* — Jones Walker LLP

(57) ABSTRACT

A fluidic hemostat agent comprising a solid hemostatic additive suspended in a silanol carrier fluid to form a heterogeneous mixture that exhibits sufficient flowability to allow for injection and proliferation, while simultaneously having sufficient adhesive and viscoelastic characteristics to remain at the application site and enable the clotting cascade time to form a thrombus. The silanol carrier fluid preferably comprises liquid silanol-bearing POSS molecules, while the solid hemostatic additive preferably is selected from the group consisting of kaolin, chitin, chitosan, cellulose, keratin pectin, acetylated glucosamine, dry fibrin, gelatin, and calcium salts. A preferred silanol species is iso-octylPOSS trisilanol having the molecular representation [(i-ocyl-$SiO_{1.5}$)$_4$(i-octyl(OH)$SiO_{1.0}$)$_3$]$_{\Sigma 7}$.

19 Claims, 9 Drawing Sheets

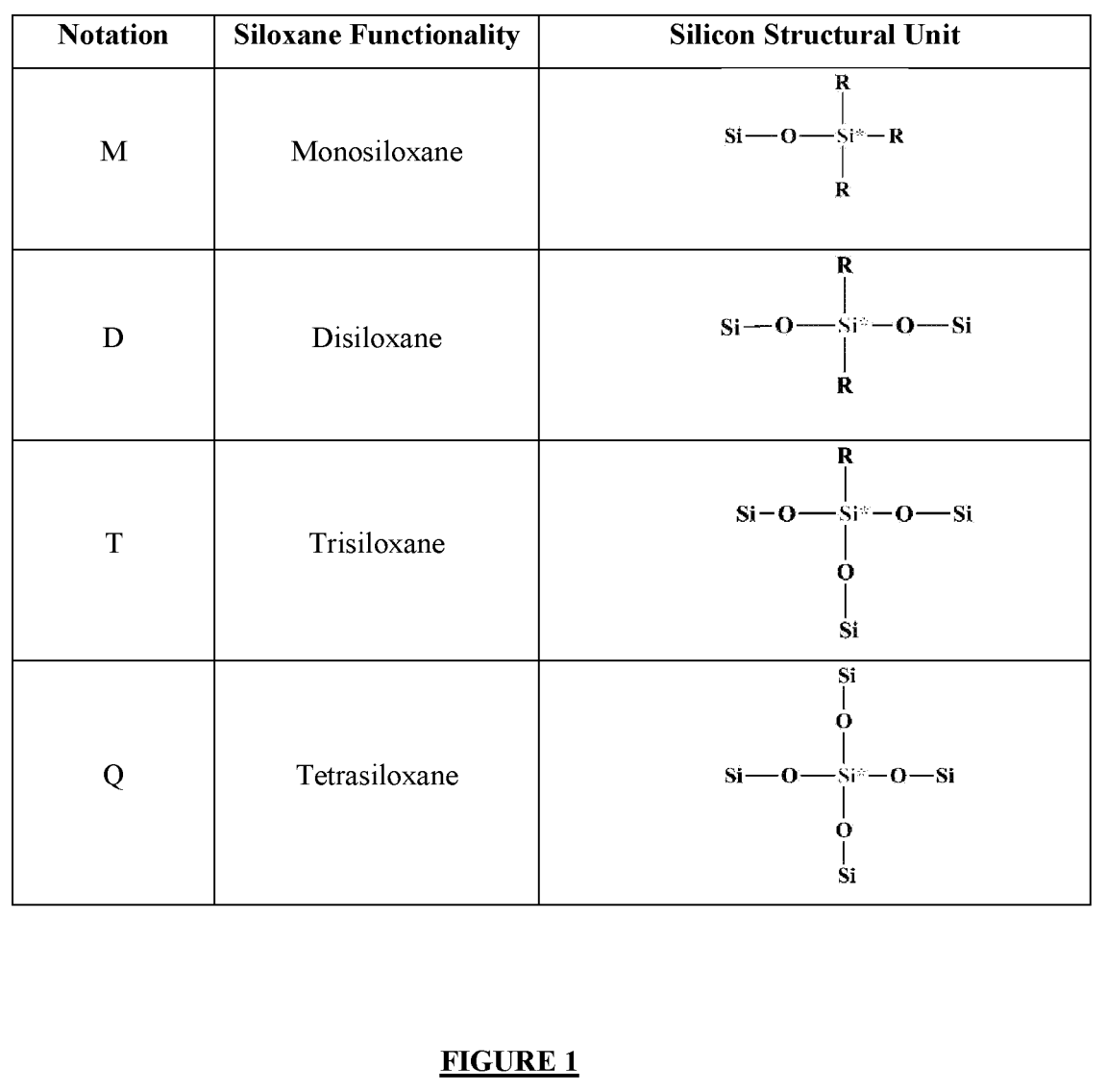

| Notation | Siloxane Functionality | Silicon Structural Unit |
|:---:|:---:|:---:|
| M | Monosiloxane | $\text{Si—O—Si}^*\text{—R}$ with R above and R below |
| D | Disiloxane | $\text{Si—O—Si}^*\text{—O—Si}$ with R above and R below |
| T | Trisiloxane | $\text{Si-O—Si}^*\text{—O—Si}$ with R above and O—Si below |
| Q | Tetrasiloxane | $\text{Si—O—Si}^*\text{—O—Si}$ with Si—O above and O—Si below |

FIGURE 1

T, D, Q Polysilanol                    Q-M Polysilanol

FIGURE 4

M₁ Monsilanol    D₂ Disilanol    T₄D₁ Disilanol

T₁ Trisilanol    T₄ Tetrasilanol    T₅ Pentasilanol

FIGURE 5

$$R = i\text{-octyl}$$

FIGURE 6

Comparative Arterial Blood Loss Totals w/o Compression over 3 Hours

☐ QuikClot     ☐ POSS-Chitin     ☐ POSS-Kaolin

POSS VISCOELASTIC HEMOSTATIC AGENTS

CROSS-REFERENCE TO RELATED APPLICATIONS

This application is a national stage application under 35 USC § 371 of PCT/US2020/025727, filed on Mar. 30, 2020, which claims the benefit of U.S. Provisional Application No. U.S. 62/826,132, filed Mar. 29, 2019, both of which are hereby incorporated by reference herein in their entirety.

BACKGROUND

A particularly challenging area of medicine is traumatic hemorrhaging and wound care. Traumatic hemorrhaging is particularly dangerous because it is always unexpected, and the presence of trained medical personnel at the time of injury is unlikely. In such events, first responders typically utilize a hemostat device or agent in order to slow or stop hemorrhaging. The capabilities of traditional trauma-hemostats, which have varied efficacies depending on the nature and type of hemorrhagic bleeds that can be encountered, are summarized in Table 1:

TABLE 1

| | Powder | Bandage | Tourniquet |
|---|---|---|---|
| Application Method | Pour/ Compress | Adhere/ Compress | Wrap/ Compress |
| External Use | Yes | Yes | Yes |
| Internal Use | No | No | No |
| Antimicrobial Function | Yes | No | No |
| Anti-debris Function | No | Yes | No |
| Visual Inspection Function | No | Some | No |
| Proliferative Function | No | No | No |

Hematology research has enabled significant improvements to traditional powders, gauze bandages, and tourniquets. The impregnation of these traditional hemostats with hemostatic agent additives has been shown to greatly improve their hemostatic activity. Known hemostatic agent additives include chitin, chitosan, cellulose, kaolin, silica, and related minerals, as well as acetylated glucosamine, dry fibrin, and gelatin. Silicate minerals are particularly well known to promote platelet activation, erythrocyte lysis (red blood cell destruction) and release of nitric oxide and peroxynitrite. The process has been attributed to both the rough edged crystallite topology of silicates (and related minerals) and to the presence of silanol functionality. Commercial uses of silicate minerals as hemostatic agents include the use of kaolin (a crystalline solid represented by the formula $Al_2Si_2O_5(OH)_4$) as the active agent in the QuikClot® hemostatic bandage manufactured by Z-Medica, LLC, and the silica encapsulation of chitosan in the WoundStat® hemostatic bandage manufactured by TraumaCure, Inc.

Known liquid hemostats include collagen, collagen-thrombin mixtures, thrombin-gelatin mixtures, thrombin-fibrinogen mixtures, aluminum chloride solutions, and aluminum sulfate solutions. These liquid hemostats have been useful in providing topical hemostasis. However, their viscosity is too low to stop or significantly reduce the rate of blood loss from a traumatic hemorrhage and thereby enable the clotting cascade time to form a thrombus. As a result, liquid hemostats are not yet commonly used in traumatic hemorrhaging events despite conceivably being able to provide several desirable attributes over traditional nonsurgical hemostatic devices. Significant potential advantages include ease of use, rapid deployment, and proliferation within a wound channel. Injectability and proliferation are highly desirable attributes as it may afford a hemostasis tool for difficult-to-access bleeding sites, such as with internal bleeding. Liquid hemostats also afford removal without dislodging of the thrombus and causing re-bleeding as frequently occurs with gauze-based devices. Additionally, liquid hemostats afford the ability to visually monitor and manage the wound as opposed to being limited to monitoring a bandage and surrounding tissue.

Polyhedral oligomeric silsesquioxanes (POSS)—a family of molecules that consist of a silica-like core surrounded by a shell of organic groups—are additives have been shown to be useful in a variety of biomedical applications such as dental restoratives, biomimetic implants, nerve conduits, intestinal tissue scaffolds, cardiac tissue, trachea scaffolds, and for drug delivery agents. The chemical composition of POSS is a hybrid intermediate between that of silica ($SiO_2$) and silicone ($R_2SiO$). The key purpose of POSS compositions is to create hybrid materials that are easy to process like polymers, yet possess the characteristics of high-use temperature and oxidation resistance like ceramics. These nanostructures have the empirical formula $R_n(SiO_{1.5})_n$, where R is a hydrogen atom or an organic functional group such as an alkyl, alkylene, acrylate, hydroxyl, or epoxide unit. Unlike silica or modified clays, each POSS molecule contains covalently bonded reactive functionalities suitable for polymerization or grafting POSS monomers to polymer chains, as well as nonreactive organic functionalities for solubility and compatibility of the POSS segments with the various polymer systems. As an additive, POSS provides enhanced compatibility between biological and man-made materials while improving surface and bulk properties.

Recent hemostatic research has shown that liquid silanol-bearing POSS molecules have efficacy in promoting rapid hemostasis. The liquid composition i-octyltrisilanol POSS in particular has been shown to have beneficial hemostatic properties. However, particularly in the cases of hemorrhagic injury to non-compressible areas of the body such as groin, trunk, armpit, neck and internal organs, there is a need for a fluidic hemostatic agent that will remain at the application site to enable the clotting cascade time to form a thrombus. An improved fluidic hemostat having viscoelastic properties is needed for such applications, as no satisfactory hemostatic treatment methods aside from immediate surgical repair are currently available.

SUMMARY

The invention disclosed herein is directed to a fluidic hemostat agent comprising a solid hemostatic additive suspended in a silanol carrier fluid. In many embodiments, the fluidic hemostat agent will be heterogeneous mixtures in either suspension or colloid form. The silanol carrier fluid may comprise polyhedral oligomeric silsesquioxanes, silsesquioxanes, silicones, and silicates such as a polyhedral oligomeric silicate composition. The solid hemostatic additive may be selected from the group consisting of kaolin, chitin, chitosan, cellulose, keratin pectin, acetylated glucosamine, dry fibrin, gelatin, or calcium salts. The fluidic hemostat agent of the present invention exhibits sufficient flowability to allow for injection and proliferation at wound sites, while simultaneously having sufficient adhesive and viscoelastic characteristics to remain at the wound site and enable the clotting cascade time to form a thrombus. The fluidic hemostat agent of the present invention may be applied to bleeding wounds, wounds that have disrupted or missing tissue, and wounds that have burn tissue. A soluble or insoluble antibacterial agent may be applied to the wound at the same time as the fluidic hemostat agent. The fluidic hemostat agent of the present invention also has utility as a post-surgical treatment tool, as the fluidic hemostat agent can be applied over sutures or other surgical closure mechanisms to further enhance hemostasis and sealing of the wound. The fluidic hemostat agent of the present invention may also provide pain relief.

In a particular embodiment exemplifying the principles of the invention, the fluidic hemostat agent comprises a solid hemostatic additive suspended in a silanol-bearing POSS fluid. The solid hemostatic additive may be selected from the group consisting of kaolin, chitin, chitosan, cellulose, keratin pectin, acetylated glucosamine, dry fibrin, gelatin, or calcium salts. In a preferred embodiment, the liquid silanol-bearing POSS molecule is a polyhedral oligomeric silsesquioxane (POSS) trisilanol, and more particularly trisilanol hepta-isoOctyl POSS (isoOctyl=2,2,4-trimethylpentyl), having the molecular composition $[(\text{i-OctylSiO}_{1.5})_4(\text{i-Octyl}(\text{OH})\text{SiO}_{1.0})_3]_{\Sigma7}$. In other embodiments, the silanol component may comprise a silsesquioxane or a silicate, such as a polyhedral oligomeric silicate (POS) composition.

BRIEF DESCRIPTION OF THE DRAWINGS

The accompanying figures, together with the detailed description below, are incorporated in and form part of the specification, serve to illustrate further various exemplary embodiments and to explain various principles and advantages in accordance with the present invention:

FIG. 1 is a table showing various molecules with siloxane (Si—O—Si*) backbones that are frequently denoted using a shorthand notation by the symbols M, D, T, and Q.

FIG. 4 depicts the structural formula of several polymeric silsesquioxane silanols.

FIG. 5 depicts the structural formula of several fragmented silsesquioxane silanols.

FIG. 6 depicts the structural formula of iso-octylPOSS trisilanol having the molecular representation $[(\text{i-ocyl-SiO}_{1.5})_4(\text{i-octyl}(\text{OH})\text{SiO}_{1.0})_3]_{\Sigma7}$.

DETAILED DESCRIPTION

Figure 2:
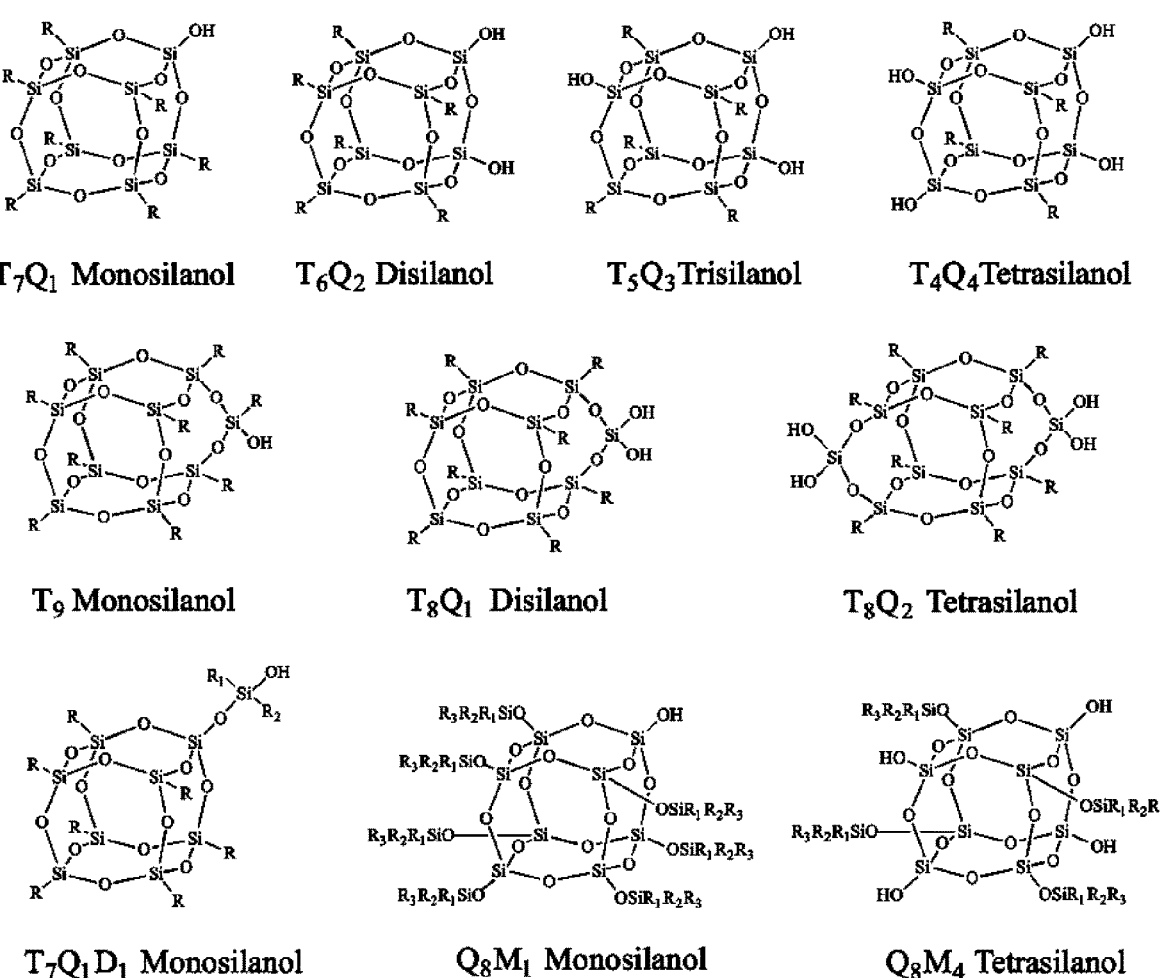
FIG. 2 depicts the structural formula of several closed cage silsesquioxane silanols.

Detailed embodiments of the present invention are disclosed herein. However, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Alternate embodiments may be devised without departing from the spirit or the scope of the invention. Further, the terms and phrases used herein are not intended to be limiting, but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

As used herein, the phrase "suspended in" is used to describe heterogeneous mixtures in both suspension and colloid form.

Figure 3:
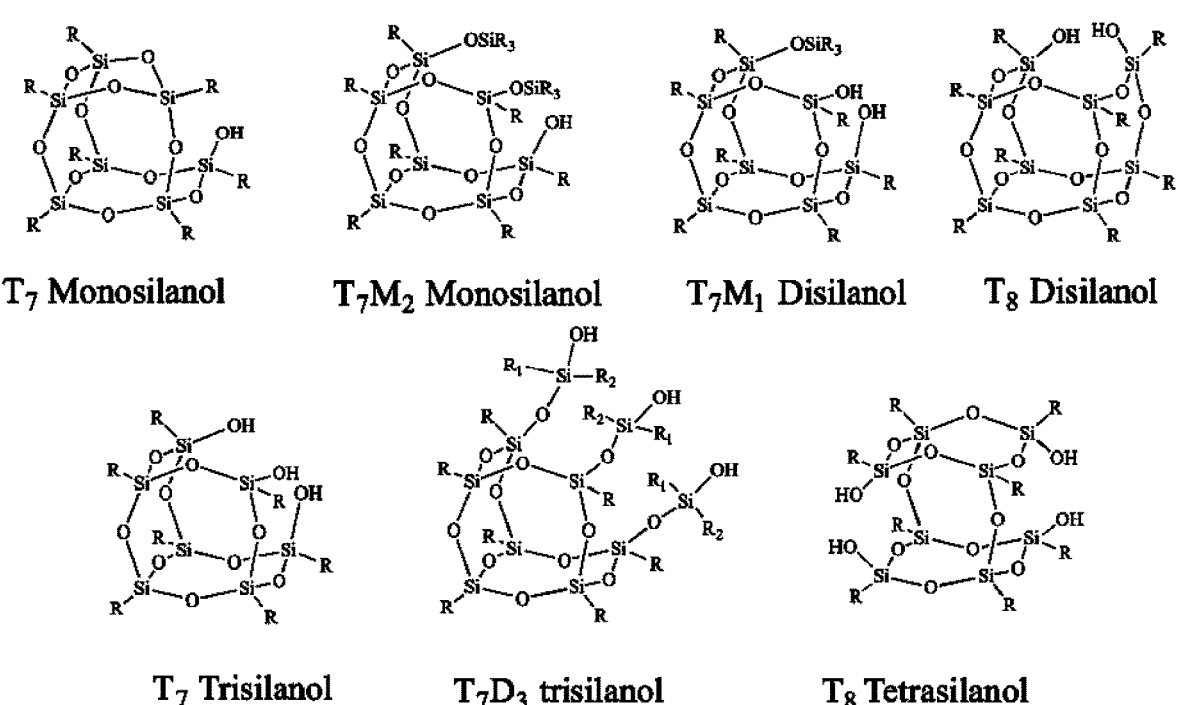
FIG. 3 depicts the structural formula of several open cage silsesquioxane silanols.
Figure 4:
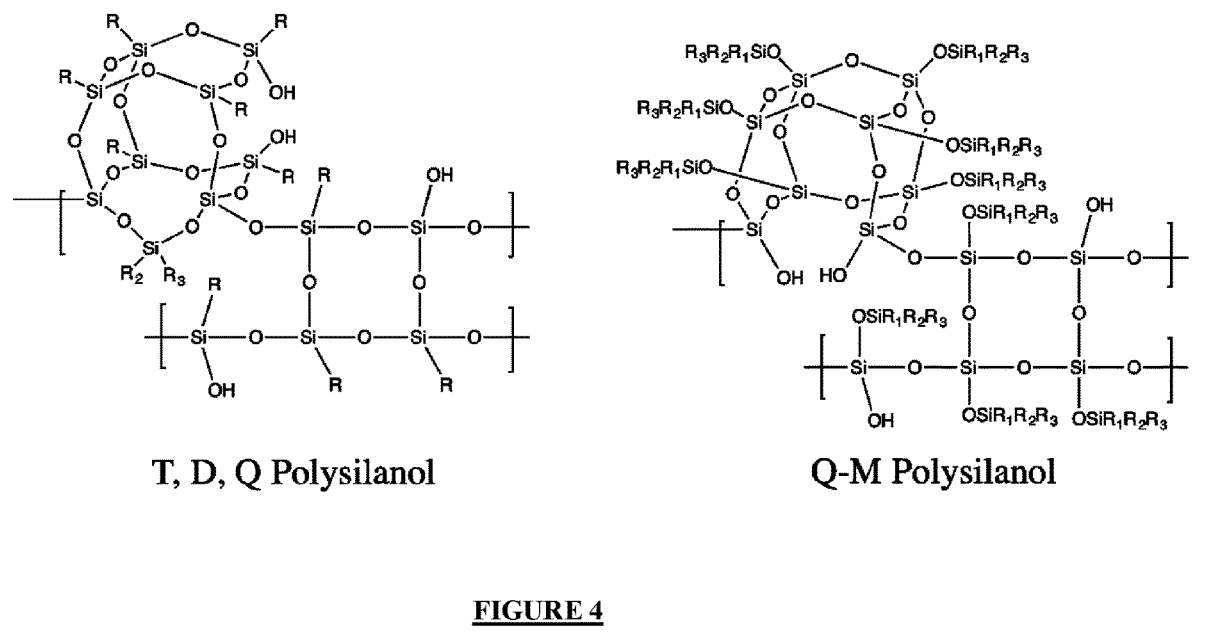
Figure 5:
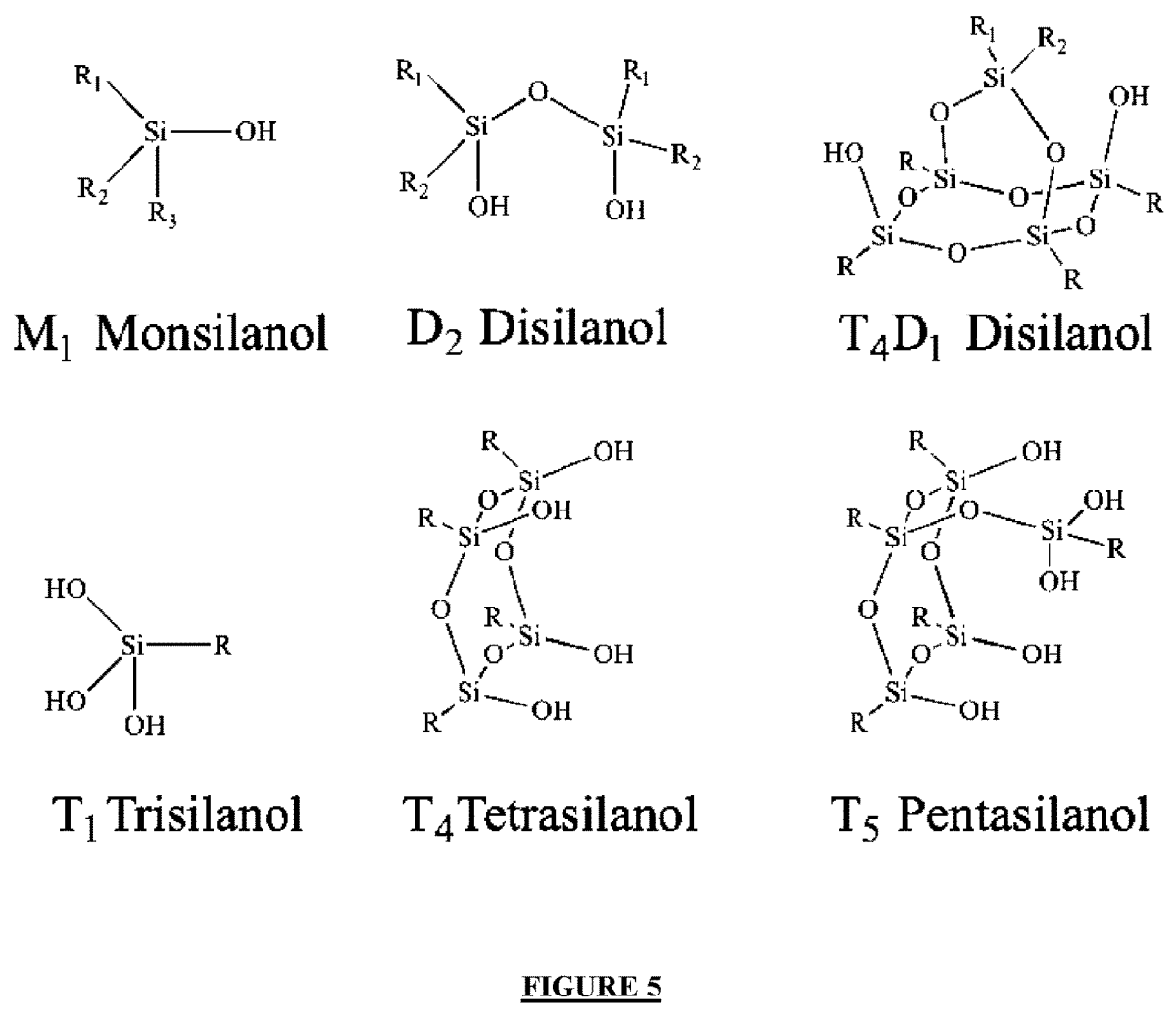

As used herein, the term "silanol" describes a functional group in silicon chemistry having the connectivity Si—OH where the OH is a hydroxyl. This functionality is found at the terminal end of a silicone or silsesquioxane polymer or molecule. In the literature for silicon compounds the terms silicone, siloxane, polysiloxane, silsesquioxane, polysilsesquioxane, polyhedral oligomeric silsesquioxane and silicate are frequently used as synonyms to describe polymers and molecules with a silicon-oxygen-silicon (Si—O—Si) backbone or framework. The environment of different structural silicon atoms is frequently denoted using a shorthand notation by the symbols M, D, T, and Q. As shown in FIG. 1, these symbols refer only to the number of silicon-oxygen (Si—O—) groups attached to the silicon atom of interest to form siloxane (Si—O—Si*) linkages. The symbol M represents a silicon atom having one Si—O—Si linkage and three organic R groups and is typically found at the terminal end of a silicone or silsesquioxane polymer or molecule. The D symbol represents a silicon atom with two Si—O—Si linkages and two organic groups and is the unit, which makes up linear silicones or polysiloxanes. The T symbol represents a silicon atom having three Si—O—Si linkages and one organic group and typically provides branch points in a silicone or silsesquioxane polymer or molecule. The Q symbol represents a silicon atom having four Si—O—Si linkages and is unique, as it contains no organic R group bound to the central silicon. Q-type silicon atoms are typically branch points in a silicone or silsesquioxane polymer or molecule. The chemistry of silanols is highly diverse and a nearly infinite variety of M, D, T, and Q compositional and structural combinations are possible. Included among these compositions are wholly closed-cage silsesquioxane silanols (see FIG. 2); open cage silanols (see FIG. 3); polymeric silanol silsesquioxanes (see FIG. 4); and fragmented silanols (see FIG. 5). For each silanol molecule the organic group (R) is defined as an organic substituent (H, cyclic or linear aliphatic or aromatic groups that may additionally contain functionalities such as alcohols, ethers, acids, esters, ketones, amines, olefins, halides, sulfides, silicones, as well as fluorinated and nonfunctional aliphatic, olefinic, or aromatic groups).

The invention disclosed herein is generally directed to a fluidic hemostat agent comprising a solid hemostatic additive suspended in a silanol carrier fluid to form a heterogeneous mixture that exhibits sufficient flowability to allow for injection and proliferation, while simultaneously having sufficient adhesive and viscoelastic characteristics to remain at the application site and enable the clotting cascade time to form a thrombus. The silanol carrier fluid preferably comprises liquid silanol-bearing POSS molecules, while the solid hemostatic additive preferably is selected from the group consisting of kaolin, chitin, chitosan, cellulose, keratin pectin, acetylated glucosamine, dry fibrin, gelatin, and calcium salts. For purposes of the present invention, a preferred silanol species is the T-type POSS trisilanol iso-Octyl with the molecular representation $[(\text{i-ocylSiO}_{1.5})_4(\text{i-octyl(OH)SiO}_{1.0})_3]_{\Sigma7}$ (referred to herein as "iso-octylPOSS trisilanol" or "i-octylPOSS trisilanol") due to its high viscosity and high equivalent weight of silanol groups. A related and higher viscosity T-type POSS trisilanol is the trisilanol octadecyl POSS $[(\text{octadecylSiO}_{1.5})_4(\text{octadecyl}(\text{OH})\text{SiO}_{1.0})_3]_{\Sigma7}$. However, other silanol species may be utilized with the fluidic hemostat agent described herein.

Figure 6:
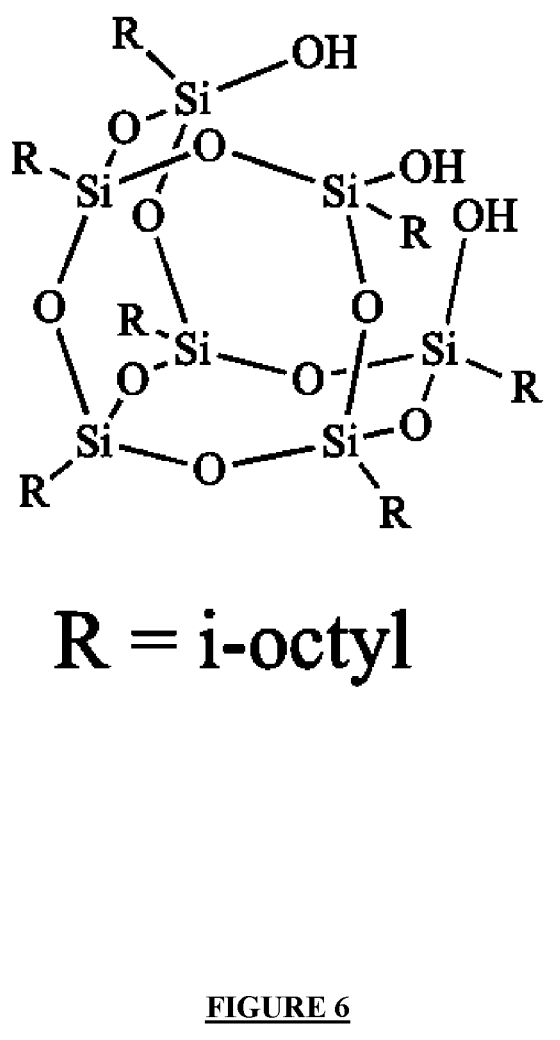

The representative structure of the liquid silanol-bearing POSS molecule i-octylPOSS trisilanol is shown in FIG. 6. The i-octylPOSS trisilanol is a hybrid molecule with an inorganic silsesquioxane at the core, seven hydrophobic, organic isooctyl groups attached at the corners of the cage and three active silanol functionalities. It is a liquid over the temperature range from −40° C. to 250° C., which enables easy application, adhesion, and proliferation within a wound. The silanol characteristic of i-octylPOSS trisilanol provides for biological compatibility, and it is also believed to contribute to the compatibility of silanol-bearing POSS molecules with the known solid hemostatic additives kaolin, chitin, chitosan, cellulose, keratin pectin, acetylated glucosamine, dry fibrin, gelatin, and calcium salts. The ability of i-octylPOSS trisilanol to function as a carrier fluid for these known solid hemostatic additives beneficially enables these otherwise solid hemostatic agents to exhibit the beneficial features of liquid hemostatic agents, namely injectability and proliferation. While the silanol groups of silanol-bearing POSS molecules, and in particular i-octylPOSS trisilanol, can also serve as carriers and platelet activators, they do not lyse erythrocytes. This renders the silanol useful and active in achieving coagulation, thereby further enhancing the overall hemostatic activity of the fluidic hemostat agent mixture described herein.

The promise of rigid cage structured silanols—and in particular polyhedral oligomeric silsesquioxanes—for biocompatible materials lies in their rigid shape, tailorable R group, highly dispersive nature, and ability to rationally control surface area, volume, and roughness. This control in turn affords the ability to stimulate a biological response in nanoscopic dimensions. POSS and POS chemicals contain a hollow internal cage core comprised of inorganic silicon-oxygen bonds, rigid silsesquioxane, silicate, and silicone. The exterior of the rigid core contains organic functionalities (R), which ensure compatibility and desired tailorability of the molecule with man-made and biological tissues. The desirable silanol attribute is selectively attached to the silicon-oxygen core. These and other properties and features of nanostructured chemicals are discussed in detail in U.S. Pat. Nos. 5,412,053 and 5,484,867 to Lichtenhan et al., both are expressly incorporated herein by reference in their entirety. The organic group (R) characteristic provides for biological compatibility, adhesion, and control of adhesion and liquid state properties. The nature of the R group also provides for a capability to interact with tissue and blood components. Organic groups can be hydrophobic and hydrophilic in properties and the use of such characteristics for controlling biological interactions with vesicles or cell membranes and use in wound treatment has been reported. Regarding i-octylPOSS trisilanol in particular, the R groups cause the molecule to resemble a surfactant with hydrophilic polarity at one end and hydrophobicity at the other. It does not liberate heat upon hydration and, as a clear liquid, exhibits excellent and nonmigrating wet-out adhesion toward collagen and tissue (endothelial and related tissue cells). The i-octyl groups are attributed to the tissue adhesion and this property is common to all i-octyl containing POSS molecules.

The rigid three-dimensional structure characteristic of i-octylPOSS trisilanol provides for cell binding, high surface area, volume, and viscosity control. High surface area, which is desirable in liquid hemostats for purposes of maximizing blood component interactions and subsequent coagulation, is achieved through use of small yet rigid three-dimensional components. Furthermore, the absence of crystallinity affords the i-octylPOSS trisilanol with a high oxygen permeation rate that enables rapid tissue healing and potential defense against anaerobic bacteria. The i-octylPOSS trisilanol is not cytotoxic and can be removed from tissue using dry gauze wipes, alcohol or hydrocarbons.

Viscosity control is critical for achievement of injectability and proliferation of the fluidic hemostat agent mixture, while simultaneously exhibiting sufficient viscosity to prevent run-off from the treatment site. While viscous liquids (Newtonian) such as i-octylPOSS trisilanol are desirable for use as carrier fluids, a fluidic hemostat agent that exhibits viscoelastic (non-Newtonian) properties are preferable as they typically undergo deformation and displacement from a hemorrhagic wound at a slower rate than a Newtonian fluid. This time dependent behavior is critical for the function of a fluidic hemostat agent because the rate of blood loss must be stopped (preferably) or significantly reduced to enable the clotting cascade to catch-up and form a thrombus. Additionally, a fluidic hemostat agent needs to remain at the bleeding site in a similar manner as would a gauze bandage to provide concentration of clotting components, and the viscosity or viscoelastic response of the fluidic hemostat agent must be sufficient to counter or resist the fluid force of bleeding. The force of fluid loss from a bleeding wound is highly variable and dependent on arterial pressure, wound size, and vessel diameter. Fluidic hemostat agents possessing tissue adhesion and viscosity or viscoelasticity in the range of 10-10,000 Pa·s are desirable. For non-compressible arterial hemorrhages the range of 100-10,000 Pa·s is preferable, while non-compressible venous bleeding can be arrested using viscosity ranges of 10-100 Pa·s. Frictional interactions of the solid hemostatic additives in the fluidic state can also be used to achieve the necessary viscoelasticity.

EXAMPLES

In order to prepare the fluidic hemostat agent mixtures described and tested herein, a solvent-free blending process was carried out by the addition of one or more solid hemostatic additives with i-octylPOSS trisilanol $[(\text{i-octyl-}\text{SiO}_{1.5})_4(\text{i-octyl(OH)SiO}_{1.0})_3]_{\Sigma7}$ in the desired weight percentages. All ingredients were added to a suitably sized container and blended using a high shear rotor stator mixer until a steady state of torque was achieved. During this mixing process aliquots can then be taken for assurance of viscosity and composition verification as well as hemostatic properties. Upon completion of quality verification, the resulting mixture was then added directly to syringe type containers and the containers were sealed. The filled containers were then subjected to sterilization through heat, chemical or radiation techniques.

Example 1: Viscometric Properties of Various Fluidic Hemostat Agent Mixtures The i-octylPOSS trisilanol is best described as an optically clear Newtonian fluid. Newtonian fluids do not change viscosity relative to shear rate. The molecular weight of trisilanol i-octyl POSS® at 1184 g/mol, is generally equivalent to that of common silicone oligomers. In comparison to telechelic silanol polydimethylsiloxanes, trisilanol i-octylPOSS is unique in terms of its high viscosity (27 Pa·s at 24° C.) relative to the 4.3 wt % of silanol it contains. Telechelic silanol polydimethylsiloxanes and diphenyl-siloxane-dimethyl-siloxane copolymers with equivalent silanol contents are generally low viscosity fluids Kaolin is a crystalline silicate material represented by the formula $Al_2Si_2O_5(OH)_4$. Silicate minerals are particularly well known to promote platelet activation, erythrocyte lysis (cell destruction) and release of nitric oxide and peroxynitrite. The process has been attributed to both the rough-edged crystallite topology of silicates (and related minerals) and to the presence of silanol functionality.

Figure 7:
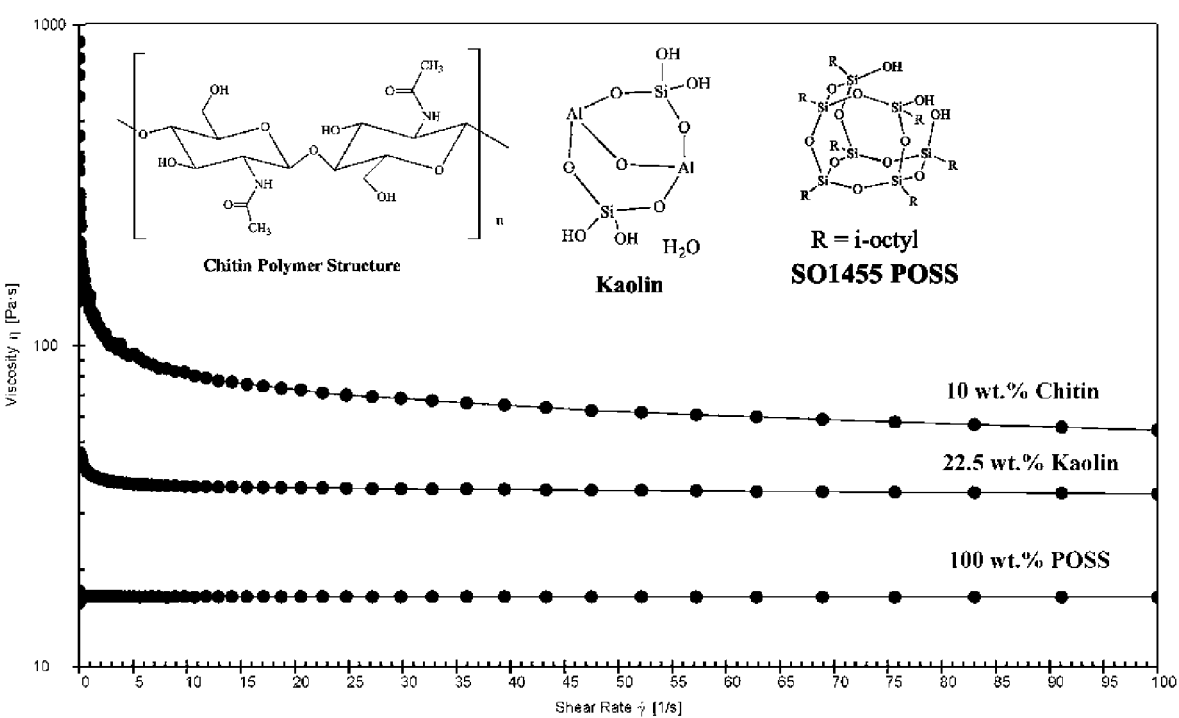
FIG. 7 is a graph depicting a comparative plot of viscosity relative to shear rate for two distinct fluidic hemostat agent mixtures formulated pursuant to the teachings of the present invention versus as a composition comprising 100% i-octylPOSS trisilanol.

Oscillatory rheology was utilized to determine the viscometric characteristics of i-octylPOSS trisilanol versus mixtures containing solid hemostatic agents suspended in in the carrier fluid, i-octylPOSS trisilanol. The solid hemostatic agents utilized for these tests were chitin and kaolin. Shear sweep measurements of viscosity at 37° C. over the range of $0.01\text{-}100 \text{ s}^{-1}$ were deemed adequate to assess reproducibility of the hemostat agent mixtures. FIG. 7 provides a comparative plot of viscosity relative to shear rate for two distinct fluidic hemostat agent mixtures as compared to a composition comprising 100% i-octylPOSS trisilanol.

The addition of 22.5 wt % kaolin to 77.5 wt % i-octylPOSS trisilanol changed the rheological properties of the i-octylPOSS trisilanol. Whereas i-octylPOSS trisilanol is a Newtonian fluid, the mixture of i-octylPOSS trisilanol and kaolin is a non-Newtonian, viscoelastic fluid. It is non-Newtonian attributes are evidenced by a reduction of viscosity relative to shear rate. The shear thinning behavior is useful as it enables the hemostat to be syringable or pourable yet to remain in place once deposited onto a wound. Desirably, the viscosity of this hemostat can be controlled simply by increasing or decreasing the amount of kaolin incorporation.

A similar viscosity test was performed using chitin as the solid hemostatic additive. The addition of 10 wt % chitin to 90 wt % of i-octylPOSS trisilanol changed the rheological properties of the i-octylPOSS trisilanol, with the mixture of i-octylPOSS trisilanol and chitin exhibiting non-Newtonian properties. The resultant hemostat agent mixture is a syringable and pourable liquid with viscoelastic characteristics that are further enhanced above that demonstrated when kaolin was used as the solid hemostatic additive. In particular, the viscosity at a shear rate of $0\text{-}2 \text{ s}^{-1}$ is 50× higher than for the i-octylPOSS trisilanol component alone and can be controlled simply by increasing or decreasing the amount of chitin incorporation.

Example 2: Venous Hemostatic Activity

Fluid loss and hemostasis of venous injuries were shown to be treatable by using a fluidic hemostat agent comprising a solid hemostatic additive suspended in the carrier fluid, i-octylPOSS trisilanol. The tested solid hemostatic additives included chitosan, cellulose, silica, acetylated glucosamine, dry fibrin, and gelatin. For the following tests, each fluidic hemostat agent mixture comprised 10 wt % of solid hemostatic additive suspended in 90 wt % of i-octylPOSS trisilanol.

In an adult human volunteer, six incisions were made through the skin to the hypodermis level. Sustained bleeding was verified for 10 seconds at each incision site, and then each of the six fluidic hemostat agent mixtures were applied to one of the six incisions. For each incision, hemostasis was achieved within 10-20 seconds without the application of compression to the wound. Under compressive conditions hemostasis was achieved within 3-5 seconds. A traditional scab was not observed, and the excess hemostat agent and associated clotted blood could be removed using a gauze tissue without re-bleeding. All of the incisions treated with the fluidic hemostat agent mixtures were observed to heal approximately 20% faster when compared to the healing rate of a non-treated control. None of the wound were observed to result in infection, and the wounds treated with the fluidic hemostat agent mixtures did not produce significant formation of oriented scar tissue.

Example 3: Junctional Artery Hemostatic Activity

Fluid loss and hemostasis of arterial injuries were shown to be treatable by using a fluidic hemostat agent comprising a solid hemostatic additive suspended in the carrier fluid, i-octylPOSS trisilanol. Large diameter, animal femoral arteries were utilized as test subjects to evaluate and compare hemorrhage control of a widely utilized, kaolin-infused gauze bandage manufactured by Z-Medica, LLC and marketed under the tradename QuikClot® versus two fluidic hemostat agent mixtures utilizing chitin and kaolin, respectively, as the tested solid hemostatic additives suspended in the carrier fluid, i-octylPOSS trisilanol. For the POSS-chitin mixture, the fluidic hemostat agent comprised 10 wt % of chitin suspended in 90 wt % of i-octylPOSS trisilanol. For the POSS-kaolin mixture, the fluidic hemostat agent comprised 22.5 wt % of kaolin suspended in 77.5 wt % of i-octylPOSS trisilanol.

Figure 8:
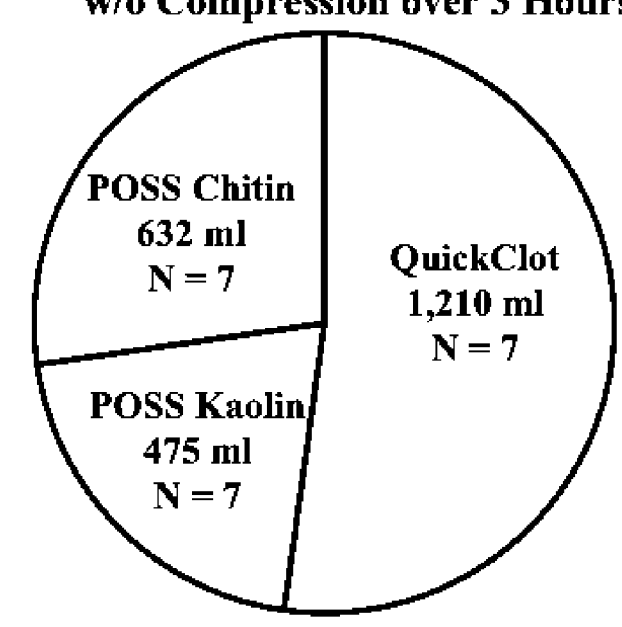
FIG. 8 is a chart depicting comparative arterial blood loss totals lost over a 3-hour period for arterial incisions treated with a kaolin-infused bandage versus two distinct fluidic hemostat agent mixtures formulated pursuant to the teachings of the present invention.

FIG. 8 presents the total blood lost over a 3-hour period from animal femoral artery hemorrhages using an approved modification of the Littlejohn model. The hemorrhage was not compressed. Hemostasis was achieved only by contact between the applied hemostat with blood and surrounding tissue. Furthermore, as a test of the durability of the thrombus, the limb was fully extended and contracted twenty (20) times every thirty (30) minutes in attempt to restart bleeding.

Figure 9:
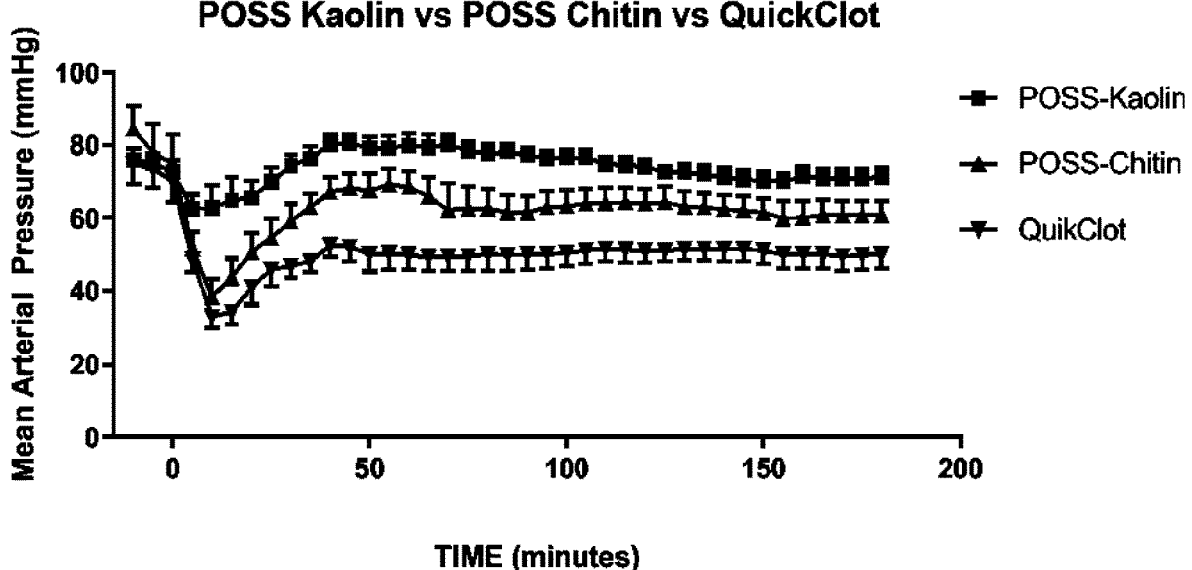
FIG. 9 is a graph depicting the mean arterial pressure over time for arterial incisions treated with a kaolin-infused bandage versus two distinct fluidic hemostat agent mixtures formulated pursuant to the teachings of the present invention.

The comparison of the total blood loss over 3 hours for seven animals per hemostat revealed that the POSS⁻kaolin mixture exhibited 60% less blood loss than the kaolin-infused gauze bandage. The POSS⁻chitin mixture exhibited 48% less blood loss than the kaolin-infused gauze bandage. Once a thrombus was formed, hemostasis was maintained throughout the 3-hour observation period and even during periods of limb movement period. Surgical literature indicates that re-bleed pressures occur within the range of 60-65 mm Hg of Mean Arterial Pressure (MAP). All of the hemostasis experiments were carried out at or above 65 mm Hg of Mean Arterial Pressure (MAP). A plot of MAP for the data sets is shown in FIG. 9. Based upon surgical observations, the upper limit of mean arterial pressure tolerance for the thrombus was within the broad range of 65-80 mm Hg. The testing confirmed that a fluidic hemostat agent could effectively address complex junctional artery hemorrhages. Furthermore, the discovery that hemostasis could be achieved through the application of a fluidic hemostat agent without compression was remarkable, establishing that these fluidic hemostat agents have utility to treat non-compressive organ injuries.

Example 4: Sealing and Hemostatic Activity

Hemostasis and sealing of lung and eye injuries were shown to be treatable by using a fluidic hemostat agent comprising a solid hemostatic additive suspended in the carrier fluid, i-octylPOSS trisilanol.

Porcine lung tissue was utilized as a test subject to evaluate and compare hemorrhage control and air sealing of i-octylPOSS trisilanol alone versus two fluidic hemostat agent mixtures utilizing chitin and kaolin, respectively, as the tested solid hemostatic additives suspended in the carrier fluid, i-octylPOSS trisilanol. For the POSS-chitin mixture, the fluidic hemostat agent comprised 10 wt % of chitin suspended in 90 wt % of i-octylPOSS trisilanol. For the POSS-kaolin mixture, the fluidic hemostat agent comprised 22.5 wt % of kaolin suspended in 77.5 wt % of i-octylPOSS trisilanol.

Using an accepted porcine testing protocol, incisions were made into lung tissue. Upon visual verification of air loss and sustained bleeding, the tested hemostatic agents were applied (–3 ml) to the wound using a syringe without compression. The incision treated with i-octylPOSS trisilanol alone was observed to seal against air loss within approximately ten (10) seconds, and hemostasis was achieved within approximately thirty (30) seconds. The incision treated with the fluidic hemostatic agent mixture of i-octylPOSS trisilanol and chitin was also observed to seal against air loss (pneumostasis) within approximately ten (10) seconds, and hemostasis was achieved within approximately thirty (30) seconds. For the incision treated with the fluidic hemostatic agent mixture of i-octylPOSS trisilanol and kaolin, the incision was observed to seal against air loss within approximately ten (10) seconds, and hemostasis was achieved within approximately sixty (60) to one hundred eighty (180) seconds. Upon achievement of hemostasis or sealing of lung tissue, the hemostatic agent can be removed via wiping it away with a gauze, bandage, sponge wipe, or towel. The hemostatic agents of the present invention also are highly soluble in isopropyl alcohol or ethanol. Therefore, an especially effective method of removing the hemostatic agents from tissue and a wound is to wet a gauze pad with either of these alcohols and wipe the tissue. During this process, the thrombi will generally remain highly adherent to the tissue without resumption of air loss or re-bleeding. The removal of a hemostatic agent without re-bleeding is highly beneficial in a surgical setting as it allows for visual observation of the injury without occlusion from active bleeding and thus more detailed planning and preparation prior to permanent repair to be made via suturing and glue. Moreover, the fluidic hemostat agent of the present invention has utility as a post-surgical treatment tool, as the fluidic hemostat agent can be applied over sutures, glue, or other surgical closure mechanisms to further enhance hemostasis and sealing of the wound.

What is claimed is:

1. A fluidic hemostatic agent comprising:
   a) a silanol carrier fluid; and
   b) a solid hemostatic additive suspended in the silanol carrier fluid, wherein the solid hemostatic additive is selected from the group consisting of kaolin, chitin, chitosan, cellulose, keratin pectin, acetylated glucosamine, dry fibrin, gelatin, or calcium salts;

c) wherein the fluidic hemostatic agent exhibits a viscosity that varies as a function of applied shear rate.

2. The fluidic hemostatic agent of claim 1, wherein the silanol carrier fluid comprises a composition selected from the group consisting of polyhedral oligomeric silsesquioxanes, silsesquioxanes, silicones, and silicates.

3. The fluidic hemostatic agent of claim 1, wherein the silanol carrier fluid comprises i-octylPOSS trisilanol.

4. The fluidic hemostatic agent of claim 3, wherein the solid hemostatic additive comprises cellulose.

5. The fluidic hemostatic agent of claim 3, wherein the solid hemostatic additive comprises kaolin.

6. The fluidic hemostatic agent of claim 4, wherein the fluidic hemostatic agent comprises between 1 wt % and 45 wt % of cellulose suspended in i-octylPOSS trisilanol.

7. The fluidic hemostatic agent of claim 5, wherein the fluidic hemostatic agent comprises between 1 wt % and 50 wt % of kaolin suspended in i-octylPOSS trisilanol.

8. The fluidic hemostat agent of claim 1, wherein the fluidic hemostat agent exhibits a viscosity measured by an oscillatory rheometer in the range of 10-10,000 Pa·s at 37° C.

9. The fluidic hemostat agent of claim 1, wherein the fluidic hemostat agent exhibits a non-linear decrease in viscosity measured by an oscillatory rheometer over a shear rate in the range of 0.01-100 $s^{-1}$.

10. A fluidic hemostatic agent comprising:
    a) a silanol carrier fluid, wherein the silanol carrier fluid comprises a silanol-bearing composition selected from the group consisting of polyhedral oligomeric silsesquioxanes, silsesquioxanes, silicones, and silicates; and
    b) a solid hemostatic additive suspended in the silanol carrier fluid;
    c) wherein the fluidic hemostatic agent exhibits a viscosity that varies as a function of applied shear rate.

11. The fluidic hemostatic agent of claim 10, wherein the solid hemostatic additive is selected from the group consisting of kaolin, chitin, chitosan, cellulose, keratin pectin, acetylated glucosamine, dry fibrin, gelatin, or calcium salts.

12. The fluidic hemostatic agent of claim 10, wherein the solid hemostatic additive comprises cellulose.

13. The fluidic hemostatic agent of claim 10, wherein the solid hemostatic additive comprises kaolin.

14. The fluidic hemostatic agent of claim 12, wherein the fluidic hemostatic agent comprises between 1 wt % and 45 wt % of chitin suspended in i-octylPOSS trisilanol.

15. The fluidic hemostatic agent of claim 13, wherein the fluidic hemostatic agent comprises between 1 wt % and 50 wt % of kaolin suspended in i-octylPOSS trisilanol.

16. The fluidic hemostat agent of claim 10, wherein the fluidic hemostat agent exhibits a viscosity measured by an oscillatory rheometer in the range of 10-10,000 Pa·s at 37° C.

17. The fluidic hemostat agent of claim 10, wherein the fluidic hemostat agent exhibits a non-linear decrease in viscosity measured by an oscillatory rheometer over a shear rate in the range of 0.01-100 $s^{-1}$.

18. A process for treating a hemorrhaging wound site, the process comprising:
    a) providing a fluidic hemostatic agent comprising a solid hemostatic additive suspended in i-octylPOSS trisilanol, wherein the solid hemostatic additive is selected from the group consisting of kaolin, chitin, chitosan, cellulose, keratin pectin, acetylated glucosamine, dry fibrin, gelatin, or calcium salts, wherein the fluidic hemostatic agent exhibits a viscosity that varies as a function of applied shear rate; and b) applying the fluidic hemostatic agent mixture to the wound site.

19. The process of claim 18, wherein the hemorrhaging wound site is an internal artery or organ, and wherein the step of applying the fluidic hemostatic agent mixture to the wound site comprises injecting the fluidic hemostatic agent through a syringe.

5

\* \* \* \* \*